United States Patent
Mishra et al.

(10) Patent No.: US 8,184,767 B2
(45) Date of Patent: May 22, 2012

(54) IMAGING SYSTEM AND METHOD WITH SCATTER CORRECTION

(75) Inventors: Debasish Mishra, Bangalore (IN); William Robert Ross, Rotterdam, NY (US); Thomas James Batzinger, Burnt Hills, NY (US); Manoharan Venugopal, Bangalore (IN); Forrest Frank Hopkins, Cohoes, NY (US); Nityanand Gopalika, State College, PA (US); Vamshi Krishna Reddy Kommareddy, Bangalore (IN); Rajashekar Venkatachalam, Bangalore (IN); Prasad Thapa, Bangalore (IN)

(73) Assignee: General Electric Company, Niskayuna, NY (US)

(*) Notice: Subject to any disclaimer, the term of this patent is extended or adjusted under 35 U.S.C. 154(b) by 234 days.

(21) Appl. No.: 12/331,549

(22) Filed: Dec. 10, 2008

(65) Prior Publication Data

US 2010/0140485 A1    Jun. 10, 2010

(51) Int. Cl.
    A61B 6/00 (2006.01)
(52) U.S. Cl. .................. 378/7; 378/6; 378/154
(58) Field of Classification Search .............. 378/7, 154
    See application file for complete search history.

(56) References Cited

U.S. PATENT DOCUMENTS

| | | | | |
|---|---|---|---|---|
| 4,549,307 A | * | 10/1985 | Macovski | 378/145 |
| 4,651,002 A | * | 3/1987 | Anno | 250/336.1 |
| 4,656,650 A | * | 4/1987 | Kikuchi et al. | 378/7 |
| 4,727,562 A | * | 2/1988 | Belanger | 378/98.4 |
| 5,050,198 A | * | 9/1991 | Honda | 378/98.2 |
| 5,533,088 A | | 7/1996 | Fivez | |
| 6,175,609 B1 | * | 1/2001 | Edic et al. | 378/7 |
| 6,618,466 B1 | | 9/2003 | Ning | |
| 6,731,783 B2 | * | 5/2004 | Tsujii | 382/132 |
| 7,039,151 B2 | * | 5/2006 | Tsujii | 378/7 |
| 7,065,234 B2 | | 6/2006 | Du et al. | |
| 7,116,749 B2 | | 10/2006 | Besson | |
| 7,308,072 B2 | | 12/2007 | Ruhrnschopf | |
| 2002/0048339 A1 | * | 4/2002 | Schneider et al. | 378/7 |
| 2002/0048347 A1 | * | 4/2002 | Saito | 378/207 |

(Continued)

FOREIGN PATENT DOCUMENTS

WO  2006082557 A2  8/2006

OTHER PUBLICATIONS

Alexander L. C. Kwan, John M. Boone and Nikula Shah; "Evaluation of x-ray scatter properties in a dedicated cone-beam breast CT scanner"; Med. Phys. 32 9 . . . , Sep. 2005; 2005 Am. Assoc. Phys. Med.; 0094-2405/2005/329 . . . /2967/9/$22.50; pages from 2967-2975.

(Continued)

*Primary Examiner* — Alexander H Taningco
(74) *Attorney, Agent, or Firm* — Penny A. Clarke

(57) ABSTRACT

An imaging technique is provided for acquiring scatter free images of an object. The technique includes acquiring a plurality of projection images of the object using a source and a detector oriented at a plurality of projection angles relative to the object, and generating a plurality of scatter free projection images by correcting the plurality of projection images based on respective ones of a plurality of stored scatter images. The scatter images are generated and stored for each of the projection angles by positioning a scatter rejection plate between the object and the detector. The technique further includes reconstructing a three-dimensional image of the object based on the scatter free projection images.

18 Claims, 6 Drawing Sheets

U.S. PATENT DOCUMENTS

| | | | |
|---|---|---|---|
| 2002/0094061 A1* | 7/2002 | Martens | 378/86 |
| 2003/0026386 A1* | 2/2003 | Tang et al. | 378/154 |
| 2004/0264629 A1* | 12/2004 | Tang | 378/7 |
| 2005/0025278 A1* | 2/2005 | Hagiwara | 378/7 |
| 2005/0243963 A1* | 11/2005 | Ghelmansarai et al. | 378/7 |
| 2006/0008046 A1* | 1/2006 | Ruhrnschopf | 378/7 |
| 2006/0088140 A1 | 4/2006 | Fahrig et al. | |
| 2006/0120507 A1 | 6/2006 | Brunner et al. | |
| 2007/0104310 A1* | 5/2007 | Nottling et al. | 378/4 |
| 2007/0242794 A1* | 10/2007 | Stanton et al. | 378/5 |

OTHER PUBLICATIONS

Masahiro Endo, Shinichiro Mori and Takanori Tsunoo; "Magnitude and effects of x-ray scatter in a 256-slice CT scanner"; 2006 Am. Assoc. Phys. Med; Received Aug. 3, 2005; revised Jun. 23, 2006; accepted for publication Jun. 24, 2006; published Aug. 29, 2006; pages from 3359-3368.

* cited by examiner

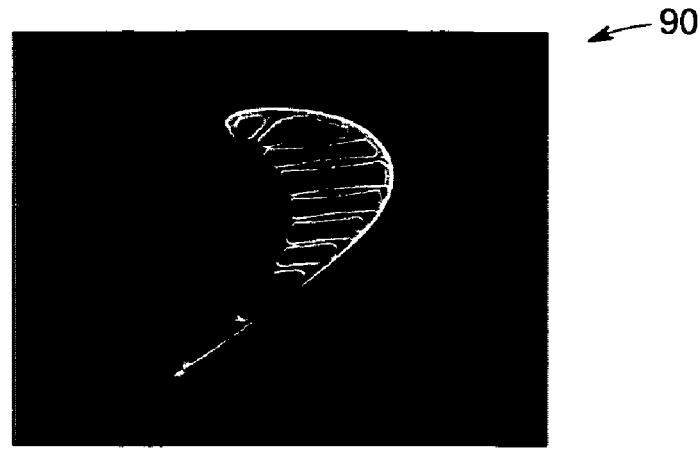
FIG. 7
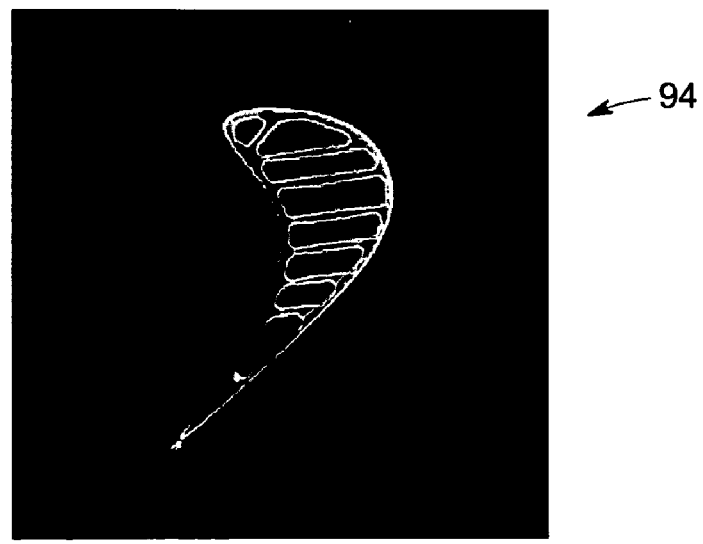

IMAGING SYSTEM AND METHOD WITH SCATTER CORRECTION

BACKGROUND

The invention relates generally to the field of non-invasive imaging and more specifically to the field of computed tomography (CT) imaging and inspection systems. In particular, the invention relates to a technique for correcting scatter from digital radiographs acquired via volumetric computed tomography (VCT) systems.

Inspection of objects is of vital importance in manufacturing and repair industries. Various types of inspection systems, such as computed tomography (CT), coordinate measuring machines (CMM), laser-based profilometry, light gauge, infrared and others, are used in industrial inspection processes for a wide variety of applications. For example, these inspection systems may be used for measuring dimensions or for identifying defects in manufactured parts, such as turbine blades. Each of these inspection systems has its advantages and disadvantages. Modalities such as CMM and laser-based profilometry typically measure external surfaces with high accuracy, but cannot measure internal features unless the object is cut open. To date, CT is the most versatile of the measurement/inspection systems for revealing both the internal and external structures of industrial parts in a non-destructive manner. Because of their ability to provide internal as well as external measurements, CT based techniques may facilitate processes such as reverse engineering, rapid prototyping, casting simulation and validation, tire development, first article inspection, ceramic porosity inspection, process validation, parts qualification and defect detection, among others. However, CT based techniques may also have certain limitations, which may deter their widespread use.

For example, volumetric computerized tomography (VCT) imaging for industrial applications (e.g., imaging of metallic parts) typically provides unsatisfactory images having image artifacts due to radiation-matter interaction based artifacts, scanner based artifacts, reconstruction techniques based artifacts, and so forth. The radiation-matter interaction based artifacts may further include beam hardening artifacts and artifacts due to x-ray scatter radiations. Scatter radiation in the projection images reduces the contrast of the projection images, produces degradation of or blurs sharp features of the object in the generated volume images, and reduces the accuracy of metrology applications and the detectability of smaller features. Scatter radiation is a strong function of the imaging parameters such as the object under imaging, beam spectrum used, geometrical distances, and the surrounding medium. Due to various dependencies in the imaging parameters, an accurate estimation of the scatter signal content in projection imaging is challenging. Physics-based models are often used for predicting scatter content in x-ray images, however they are time consuming and predict only scatter arising out of the object under scanning, provided the material properties are known.

There exist different techniques for scatter measurement and scatter correction in acquired projection images. For example, one popular scatter measurement technique employs a beam stopper located between the radiation source and the object being scanned in a VCT system to measure the scatter at a corresponding location. However, most currently known techniques primarily address the object scatter and involve time-consuming computer simulations.

As manufacturing tolerances become tighter, there is a corresponding increase in the demands for metrology techniques for maintaining the tolerances. The need for quality and performance testing has become an integral part of the production or manufacturing process. Thus, in order to improve CT inspection accuracy and efficiency, more effective methods are needed for removing scatter radiation related artifacts. Accordingly, a need exists for a measurement technique that is relatively inexpensive, versatile and programmable for different applications and that requires low maintenance.

It is therefore desirable to provide an improved scatter measurement and correction technique that accurately measures scatter radiation in the projection images and removes the same from the projection images, thereby improving the VCT image quality. It is also desirable that the improved scatter measurement and correction technique is inexpensive and computationally efficient and time efficient, thereby increasing the throughput of the VCT system.

BRIEF DESCRIPTION

Briefly, in accordance with one aspect of the present invention, a method is provided for imaging an object. The method provides for acquiring a first projection image of the object using a source and a detector. The first projection image includes a primary image of the object and a scatter image of the object. The method also provides for positioning a scatter rejection plate between the object and the detector, and acquiring a second projection image of the object with the scatter rejection plate disposed between the object and the detector. The second projection image includes the primary image of the object. The method further provides for generating a scatter image of the object based on the first projection image and the second projection image, and storing the scatter image of the object for subsequent imaging. Systems and computer programs that afford such functionality may be provided by the present invention.

In accordance with another aspect of the present invention, a method is provided for imaging an object. The method provides for acquiring a plurality of projection images of the object using a source and a detector oriented at a plurality of projection angles relative to the object, and generating a plurality of scatter free projection images by correcting the plurality of projection images based on respective ones of a plurality of stored scatter images. The scatter images are generated and stored for each of the projection angles by positioning a scatter rejection plate between the object and the detector. The method further provides for reconstructing a three-dimensional image of the object based on the scatter free projection images. Here again, systems and computer programs affording such functionality may be provided by the present invention.

In accordance with an additional aspect of the present invention, a volumetric CT system is provided for imaging an object. The volumetric CT system includes a source and a detector configured to move with respect to the object. The detector is further configured to acquire a plurality of projection images of the object from a plurality of projection angles. The volumetric CT system further includes a processor configured to generate a plurality of scatter free projection images by correcting the projection images based on respective stored scatter images, and to reconstruct a three-dimensional image of the object based on the scatter free projection images. The scatter images are generated and stored for each of the projection angles by employing a scatter rejection plate positioned between the object and the detector.

DRAWINGS

These and other features, aspects, and advantages of the present invention will become better understood when the following detailed description is read with reference to the accompanying drawings in which like characters represent like parts throughout the drawings, wherein:

FIG. 7 depicts, for a turbine fan blade, uncorrected image and scatter corrected images by employing the control logic of FIG. 6.

DETAILED DESCRIPTION

The present techniques are generally directed to computed tomography (CT) imaging resulting in improved image quality. Such imaging techniques may be useful in a variety of imaging contexts, such as medical imaging, industrial metrology and inspection, security screening, baggage or package inspection, and so forth. Moreover, such imaging techniques may be employed in a variety of imaging systems, such as CT systems, tomosynthesis systems, X-ray imaging systems, and so forth. Though the present discussion provides examples in an industrial inspection context with respect to CT systems resulting in improved measurement and inspection accuracy, one of ordinary skill in the art will readily apprehend that the application of these techniques in other contexts and in other systems is well within the scope of the present techniques.

Figure 1:
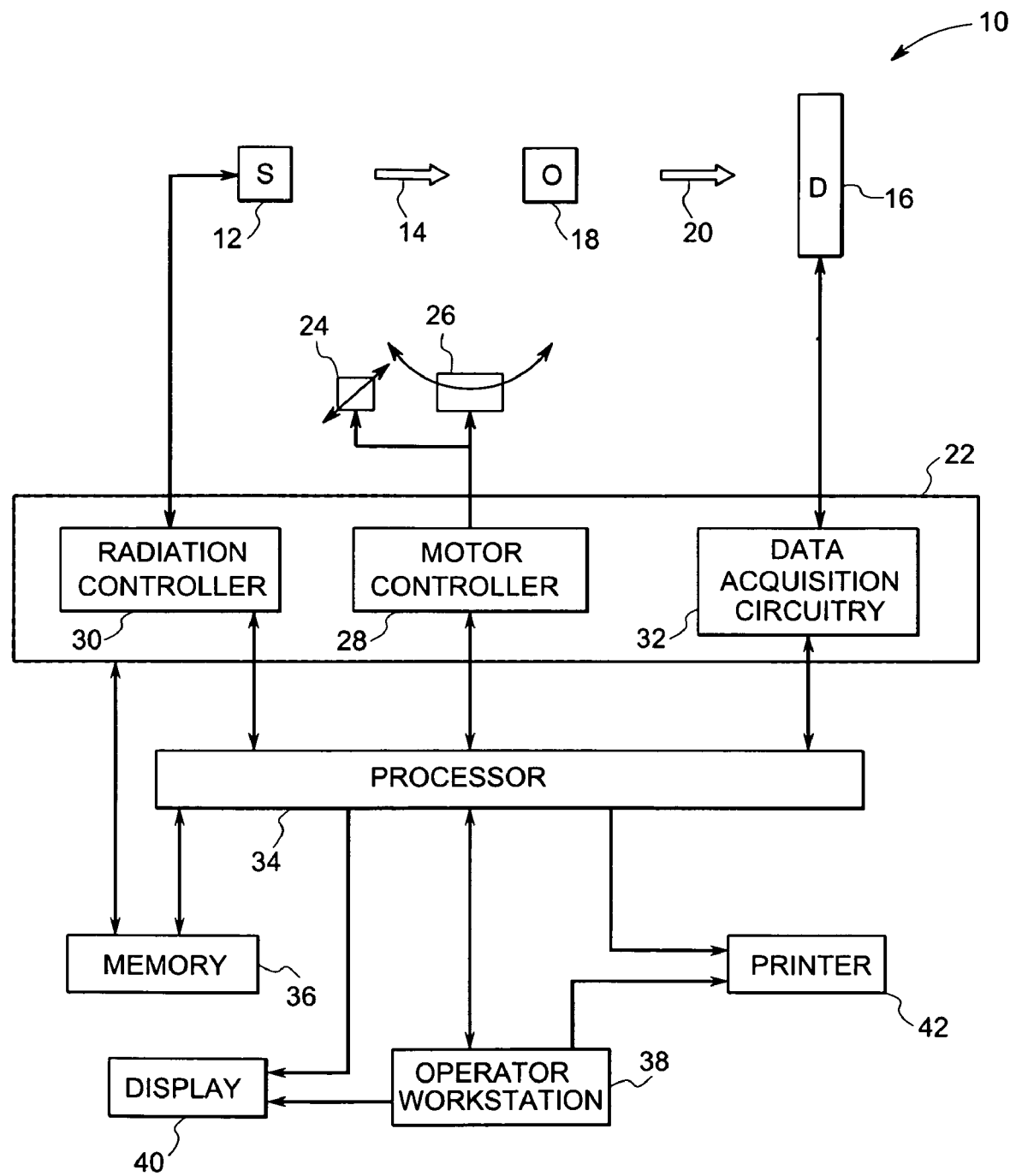
FIG. 1 depicts an exemplary flat panel VCT system for imaging an object in which aspects of the present technique may be practiced.

Referring now to FIG. 1, an imaging system 10 for use in accordance with the present technique is illustrated. In the illustrated embodiment, the imaging system 10 is a volumetric computed tomography (VCT) system designed both to acquire image data and to process the image data for display and analysis in accordance with the present technique. In the illustrated embodiment, the imaging system 10 includes a radiation source 12, such as an X-ray source. A collimator may be positioned adjacent to the radiation source 12 for regulating the size and shape of a stream of radiation 14 that emerges from the radiation source 12.

In typical operation, the radiation source 12 projects a stream of radiation 14, such as an X-ray beam, towards a detector array 16 placed on the opposite side of the radiation source 12, relative to the imaged object. The stream of radiation 14 passes into an imaging volume in which an object 18, such as a turbine blade or other item to be imaged may be positioned. Non-limiting examples of the object 12 include industrial parts, including but not limited to turbine airfoils, blades, disks, and shafts. It should be noted that a particular region of the object 18 may be chosen by an operator for imaging so that the most useful scan of the region may be acquired.

A portion of the radiation 20 passes through or around the object 18 and impacts the detector array 16. The detector array 16 may be an area detector and is generally formed as a two-dimensional array of detection elements. In one implementation, the detector array 16 may be a flat-panel detector formed as rows and columns of detector elements that may be individually read out. Each detector element produces an electrical signal that represents the intensity of the incident radiation 20 at the detector element when the radiation 20 strikes the detector array 16. Typically, signals are acquired at one or more view angle positions around the object 18 so that a plurality of radiographic views may be collected. These signals are acquired and processed to reconstruct an image of the features internal as well as external to the object 18.

The object 18, the radiation source 12, and the detector array 16 are typically displaced relative to each other, allowing projection data to be acquired at various views relative to the object 18 if desired. For example, in one implementation, the object 18 may be positioned on a table, such as a turntable, so that the object 18 may be rotated during the examination process to expose the object 18 to the stream of radiation 14 from all sides. Alternatively, the radiation source 12 and/or the detector array 16 may be disposed on a gantry, which may be rotated around the object 18 placed on a table during the examination process. Further, in certain embodiments, components of the imaging system as well as the imaged object may be moved during the examination process to acquire projection images at different views. As the object 18 and the radiation source 12 rotate relative to each other, the detector array 16 collects data of radiation attenuation at the various view angles relative to the object 18.

Data collected from the detector array 16 then typically undergoes pre-processing to condition the data to represent the line integrals of the attenuation coefficients of the scanned objects 18. The processed data, commonly called projections, are then reconstructed to formulate a volumetric image of the scanned area, as discussed in greater detail below.

Operation of the source 12 is controlled by a system controller 22, which furnishes both power, and control signals for examination sequences. Moreover, the detector array 16 is coupled to the system controller 22, which commands acquisition of the signals generated in the detector array 16. The system controller 22 may also execute various signal processing and filtration functions, such as for initial adjustment of dynamic ranges, interleaving of digital image data, and so forth. In general, the system controller 22 commands operation of the imaging system 10 to execute examination protocols and to process acquired data. In the present context, system controller 22 may also include signal processing circuitry and other circuitry, typically based upon a general purpose or application-specific digital computer, with associated memory circuitry. The associated memory circuitry may store programs and routines executed by the computer, configuration parameters, image data, and so forth. For example, the associated memory circuitry may store programs or routines for implementing the present technique.

In the embodiment illustrated in FIG. 1, the system controller 22 is coupled to a linear positioning subsystem 24 and a rotational subsystem 26. In particular, the system controller 22 may include a motor controller 28 that controls the operation of the linear positioning subsystem 24 and the rotational subsystem 26. The rotational subsystem 26 enables the X-ray source assembly and/or the detector assembly to be rotated around the object or the patient 18. It should be noted that the rotational subsystem 26 may include a gantry. Thus, the system controller 22 may be utilized to control the rotational speed and position of the gantry. Alternatively, the rotational subsystem 26 may include a motorized turntable and the system controller 22 may be configured to rotate the motorized turntable, thereby rotating the object 18 one or multiple turns during an examination. The linear positioning subsystem 24 enables the object 18 to be displaced linearly, such as by moving a table or support on which the object 18 rests. Thus, in one embodiment, the table may be linearly moved within a gantry to generate images of particular areas of the object 18. In another embodiment (e.g., in a tomosynthesis system), the X-ray source may be moveable using a linear positioning subsystem. The detector position may be variable, but not be controlled using a positioning subsystem. It should be noted that other configurations may also be used.

Additionally, as will be appreciated by those skilled in the art, the radiation source 12 may be controlled by a radiation controller 30 disposed within the system controller 22. Particularly, the radiation controller 30 may be configured to provide power and timing signals to the radiation source 12. Further, the system controller 22 may include data acquisition circuitry 32. In this exemplary embodiment, the detector array 16 is coupled to the system controller 22, and more particularly to the data acquisition circuitry 32. The data acquisition circuitry 32 typically receives sampled analog signals from the detector array 16 and converts the data to digital signals for subsequent processing by a processor 34. Such conversion, and indeed any preprocessing, may actually be performed to some degree within the detector assembly itself.

The processor 34 is typically coupled to the system controller 24. Data collected by the data acquisition circuitry 32 may be transmitted to the processor 34 for subsequent processing and reconstruction. Reconstruction of the image may be done by general or special purpose circuitry of the processor 34. Once reconstructed, the image produced by the imaging system 10 reveals internal as well as external features of the object 18. Alternatively, an image reconstructor, that is coupled to or is a part of a processor 34, may receive sampled and digitized data from the data acquisition circuitry 32 and may perform high-speed image reconstruction to generate one or more images of the scanned object 18.

The processor 34 may include or be in communication with a memory 36. It should be understood that any type of computer accessible memory device suitable for storing and/or processing such data and/or data processing routines may be utilized by such an exemplary imaging system 10. Moreover, the memory 36 may comprise one or more memory devices, such as magnetic or optical devices, of similar or different types, which may be local and/or remote to the system 10. The memory 36 may store data, processing parameters, and/or computer programs comprising one or more routines for performing the processes described herein. Furthermore, memory 36 may be coupled directly to system controller 24 to facilitate the storage of acquired data.

The processor 34 is typically used to control the imaging system 10. The processor 34 may also be adapted to control features enabled by the system controller 22, i.e., scanning operations and data acquisition. Indeed, the system controller 22 may be implemented as hardware and software components of the depicted processor 34. In addition, the processor 34 may be configured to receive commands and scanning parameters from an operator via an operator workstation 38. For example, the operator workstation 38 may be equipped with a keyboard and/or other input devices by which an operator may control the imaging system 10. Thus, the operator may observe the reconstructed image and other data relevant to the system from processor 34, initiate imaging and so forth. Where desired, other computers or workstations may perform some or all of the functions of the present technique, including post-processing of image data simply accessed from memory device 36 or another memory device at the imaging system location or remote from that location.

A display 40 may be coupled to one of the operator workstation 38 and the processor 34 and may be utilized to observe the reconstructed image and/or to control imaging. Additionally, the scanned image may also be printed by a printer 42 which may be coupled to the processor 34 and/or the operator workstation 38, either directly or over a network. It should be further noted that the processor 34 and/or operator workstation 38 may be coupled to other output devices that may include standard or special purpose computer monitors and associated processing circuitry. Furthermore, additional operator workstations may be further linked in the imaging system 10 for outputting system parameters, requesting inspection, viewing images, and so forth, so that more than one operator may perform operations related to the imaging system 10. For example, one operator may utilize one operator workstation to image acquisition while a second operator utilizes a second operator workstation to reconstruct and/or review the results of the imaging routines. In general, displays, printers, workstations, and similar devices supplied within the imaging system 10 may be local to the data acquisition components, or may be remote from these components linked to the imaging system 10 via one or more configurable networks, such as the Internet, virtual private networks, and so forth.

The exemplary imaging system 10, as well as other imaging systems based on radiation attenuation, may employ a variety of scatter mitigation and/or correction techniques for improving the image quality. For example, the present technique employs scatter rejection plates, depicted in FIGS. 2 and 3 and represented generally at reference numeral 44, for rejecting the scatter radiation resulting from object as well as those resulting from the background in accordance with aspects of the present technique.

Figure 2:
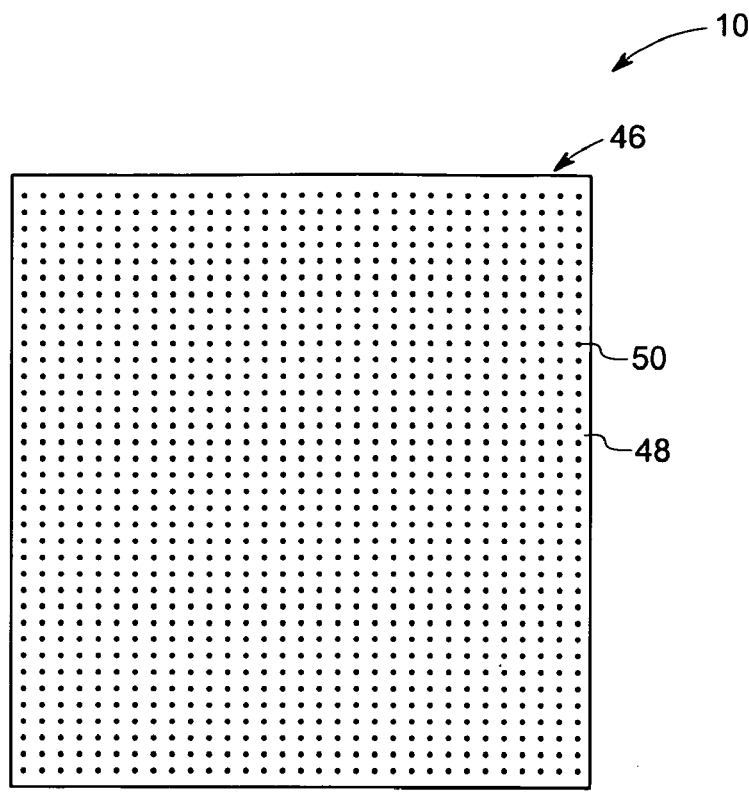
FIGS. 2 and 3 depicts scatter rejection plates in accordance with aspects of the present technique for use in flat panel VCT system of FIG. 1.
Figure 3:
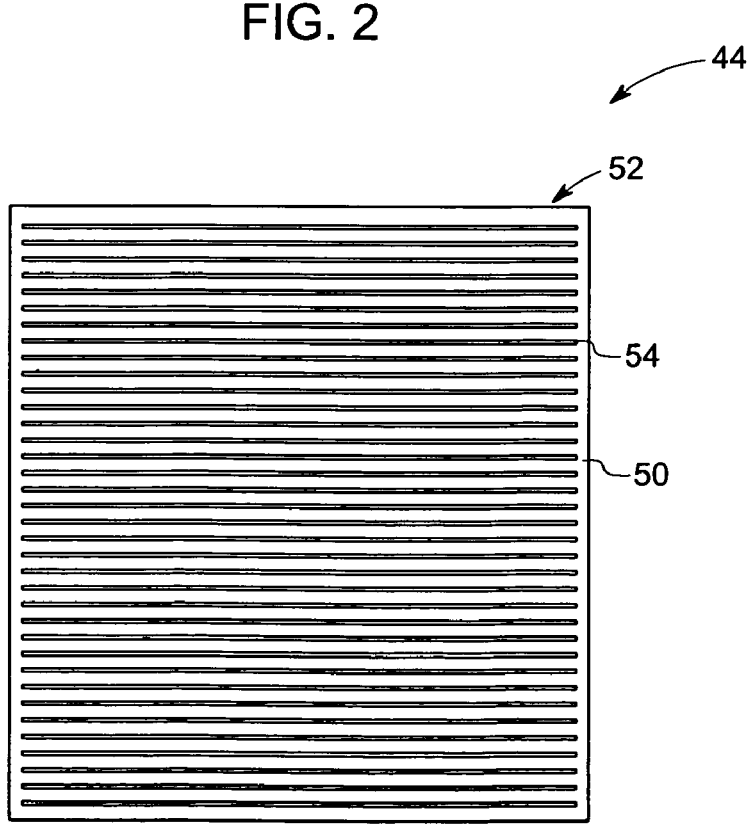

In one embodiment, the scatter rejection plate 44 may be an aperture plate 46, as illustrated in FIG. 2. The aperture plate 46 includes a plurality of sub-centimeter sized circular apertures 48 drilled in a plate 50. In certain embodiments, the apertures may be about 1-2 millimeters in diameter spaced apart at about 5 millimeters from each other (center-to-center). Alternatively, the scatter rejection plate 44 may be a collimator plate 52, as illustrated in FIG. 3. The collimator plate 52 includes a plurality of sub-centimeter sized horizontal or vertical slots 54 drilled in a plate 50. In certain embodiments, the slots may be about 1-2 millimeters in width spaced apart at about 5 millimeters from each other (center-to-center). Typically, the plate 50 is thick and made of high-density material. The high-density material may be, for example, lead, tungsten or a tungsten alloy, molybdenum, tantalum or rhenium. In certain embodiments, the plate is about 10 millimeters in thickness.

Further, various other scatter rejection plates may be designed based on the specific imaging applications and requirements, so as to optimize scatter rejection performance. For example, different variants of each of the two types of plates for scatter rejection (aperture plate and collimator plate) may be designed. In certain embodiments, if the geometry of an x-ray setup is fixed, focally aligned apertures or collimators may be designed. This provides that no primary x-ray beam deflect at wide angles. In other words, the apertures 48 or the slots 54 may be drilled at an angle parallel to the angle of incidence of the X-ray beam, so as to maximize the rejection of scatter radiation. Similarly, the aperture plate or the collimator plate may be optimized for a particular X-ray energy application. Further, it should be noted that the spacing of the apertures or collimators may be based on specific applications depending on cost and image quality requirements.

Figure 4:
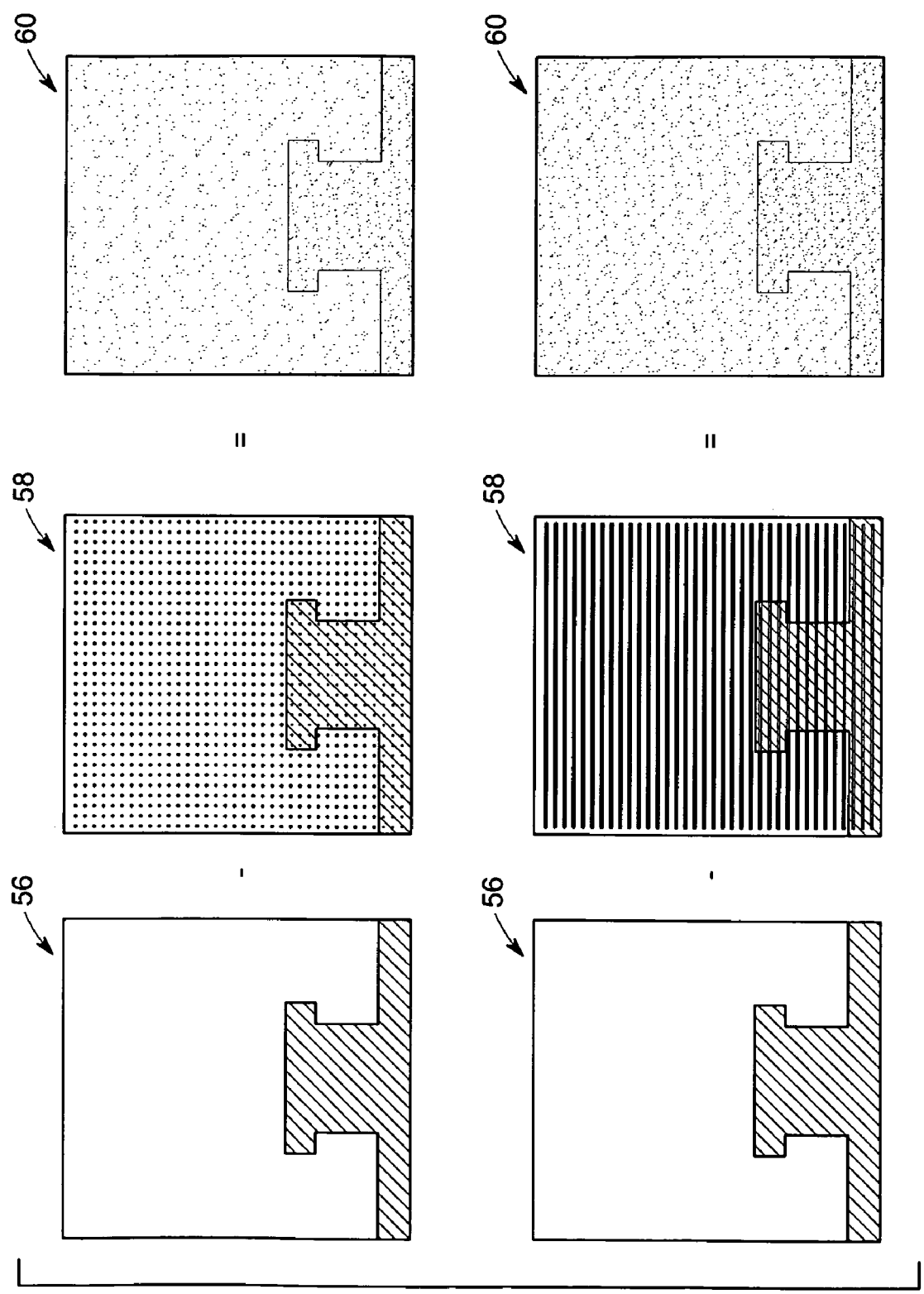
FIG. 4 depicts a schematic for generating a scatter grid image by employing the scatter rejection plates of FIGS. 2 and 3 in accordance with aspects of the present technique.

The flat panel VCT system 10 employs the scatter rejection plates 44 for generating initial scatter image of the object 18 in accordance with aspects of the present technique. For example, as illustrated in the schematic of FIG. 4, the VCT system 10 acquires a first projection image 56 of the object 18 without the scatter rejection plate 44. This first projection image 56 includes a primary image of the object as well as a scatter image of the object. The VCT system 10 then acquires a second projection image 58 of the object with the scatter rejection plate 44 positioned between the object 18 and the detector 16. This second projection image 58 includes only the primary image of the object 18. As will be appreciated by those skilled in the art, the primary image is free from any artifacts caused due to scatter radiation. Further, it should be noted that, in the second projection image, the primary image of the object 18 is formed only at certain discrete locations where measurements are obtained through the apertures or slots and is therefore dependent on the type of scatter rejection plate 44 employed to acquire the image. The illustrated embodiment depicts the primary image acquired by using aperture plate 46 as well as the primary image acquired by using collimator plate 52. The first image 56 and the second projection image 58 may also be referred as non-grid image 56 and grid image 58 respectively.

The VCT system 10 then generates the scatter image of the object at the respective one of the projection angles based on the first projection image 56 and the second projection image 58. In particular, the processor 34 subtracts the second projection image 58 from the first projection image 56 to generate a scatter grid image 60. It should be noted that acquisition of the first projection image 56 and the second projection image 58, and the generation of scatter grid image 60 are performed for each of the projection angles.

Figure 5:
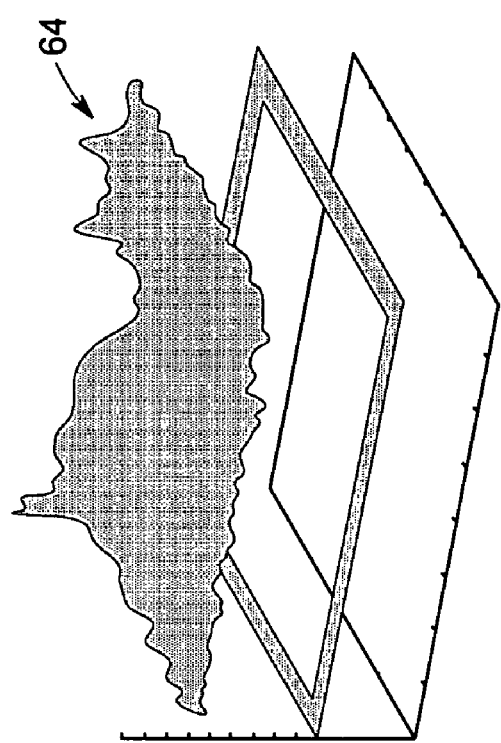
FIG. 5 depicts a schematic for interpolating the scatter grid image obtained by the technique of FIG. 4 to generate a complete scatter image in accordance with aspects of the present technique.
Figure 5:
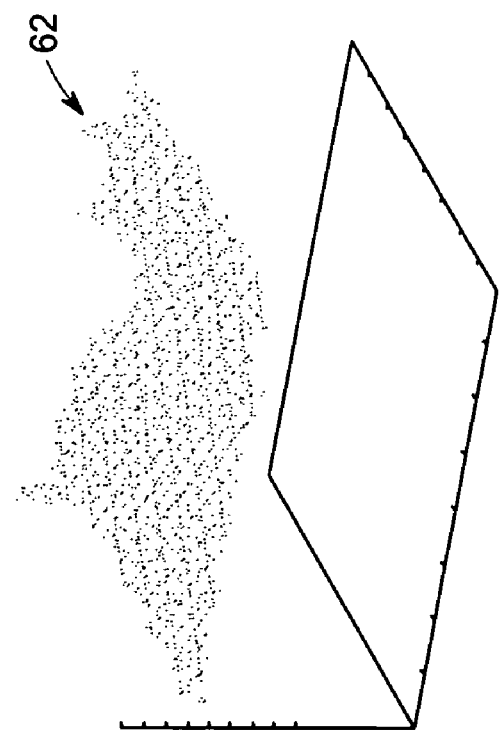

The generated scatter grid image 60 is then interpolated to generate a complete scatter image. FIG. 5 depicts an example schematic for interpolating a scatter grid image obtained by the technique of FIG. 4 to generate a complete scatter image in accordance with aspects of the present technique. As illustrated, all aperture points or centroids for the scatter grid image are first detected at step 62. It should be noted that, for the scatter grid image acquired by employing a collimator plate, the aperture points may be detected based on the required pixel resolution. The scatter grid image is then interpolated based on the detected aperture points to generate a full or complete scatter image of the object at step 64. In other words, the data points are first mapped to a regular grid and then interpolated using shape factors. As will be appreciated by those skilled in the art, any type of interpolation techniques may be employed to generate the scatter image from the scatter grid image. Non-limiting examples of the interpolation techniques include bi-linear interpolation, piecewise constant interpolation, bi-cubic interpolation, multivariate interpolation, and so forth.

As will be appreciated by those skilled in the art, a scatter image of the object is generated for each of the projection angles. The generated scatter images are stored in the memory for subsequent imaging. As will be appreciated by those skilled in the art, subsequent imaging includes acquiring projection images of the object from various projection angles and generating scatter free projection images for each projection angle based on the projection images and respective stored scatter images. The scatter free projection images are generated by correcting the projection images based on respective ones of stored scatter images. In certain embodiments, the scatter free projection images may be corrected by subtracting the respective pre-stored scatter images from the acquired projection image for each of the projection angle. It should be noted that the orientation of the object during subsequent imaging should be substantially same as it was during generation of scatter image for each projection angles. The scatter free projection images may be further processed to normalize and correct for any bad pixels in the scatter free projection images. The generated or processed scattered free projection images may then be reconstructed to generate a three-dimensional image of the object. As will be appreciated by those skilled in the art, any suitable reconstruction technique may be employed for the image reconstruction. Non-limiting examples of the reconstruction techniques include filtered back projection (FBP), iterative filtered back projection (IFBP), iterative reconstruction and/or statistical reconstruction techniques.

The exemplary imaging system 10 may generate images of the object under examination by the techniques discussed herein. In particular, as will be appreciated by those of ordinary skill in the art, control logic and/or automated routines for performing the techniques and steps described herein may be implemented by the imaging system 10 of FIG. 1, by hardware, software, or combinations of hardware and software. For example, suitable code may be accessed and executed by the processor 34 to perform some or all of the techniques described herein. Similarly application specific integrated circuits (ASICs) configured to perform some or all of the techniques described herein may be included in the processor 34 and/or the system controller 22.

Figure 6:
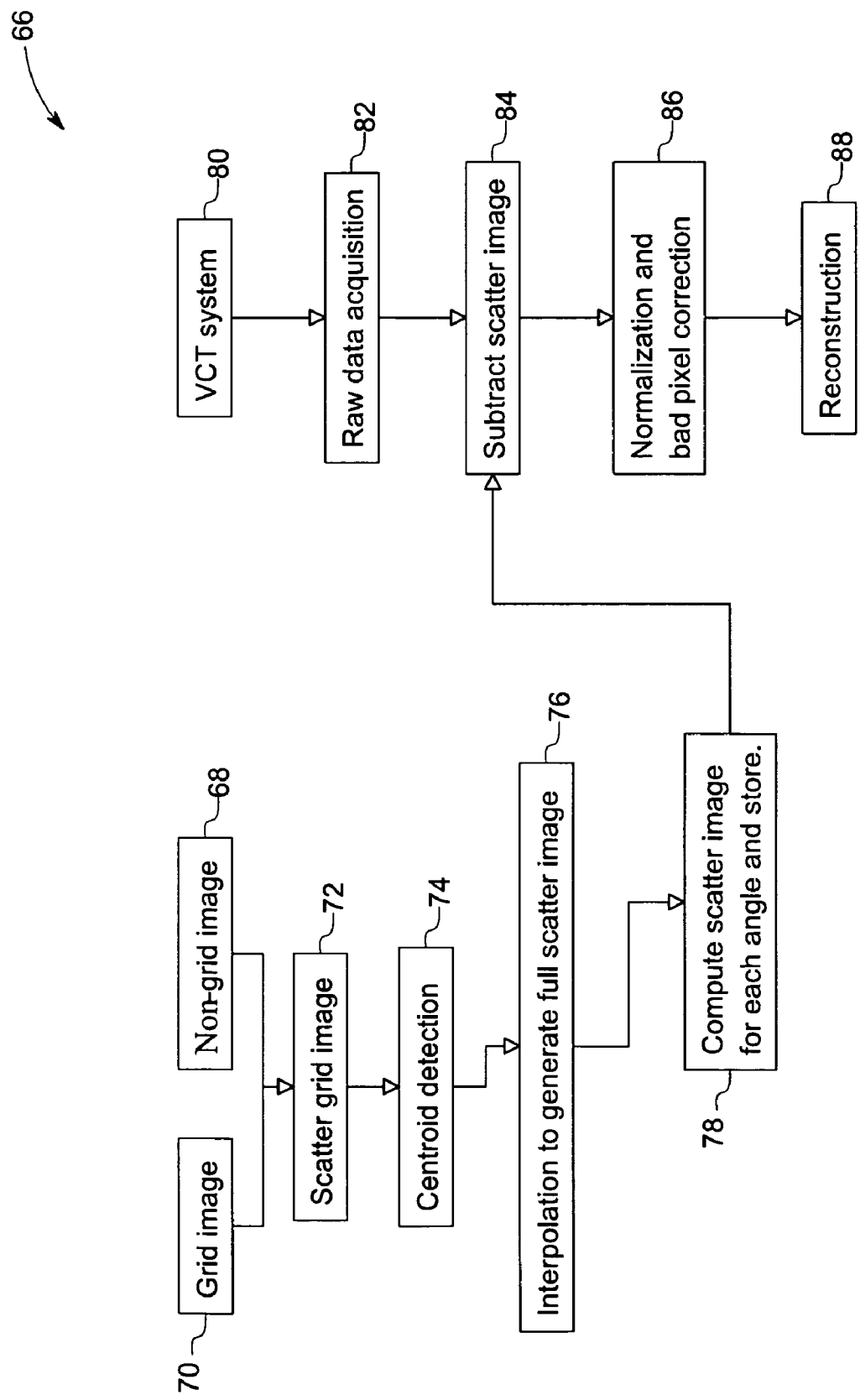
FIG. 6 depicts a control logic for inspecting an object via the flat panel VCT system of FIG. 1 by employing a scatter measurement and correction technique in accordance with aspects of the present technique.

For example, referring now to FIG. 6, exemplary control logic for inspecting an object by employing scatter measurement and correction technique on the imaging system such as flat panel VCT system 10 is depicted in accordance with aspects of the present technique. As illustrated in the flowchart 66, a non-grid image and a grid image may be acquired for a given object at multiple projection angles via the VCT system at steps 68 and 70 respectively. As discussed above, the grid image may be acquired by employing the scatter rejection plate positioned between the object and the detector. A scatter grid image is then generated based on the non-grid image and the grid image at step 72. The scatter grid image is then processed to detect multiple aperture points or centeroids at step 74. Based on the detected centeroids, the scatter grid image is then interpolated to generate a full scatter image of the given object at step 76. The process is repeated for each of the multiple projection angles and the generated scatter images for the respective projection angles are stored for subsequent imaging applications at step 78.

During subsequent imaging, the VCT system images the object at step 80 and acquires projection images of the object from various projection angles at step 82. It should be noted that, the projection images are acquired for same projection angles for which the scatter images have been generated. The scatter free projection images are then generated based on the projection images and corresponding scatter images at step 84. In one embodiment this is done by subtracting the corresponding scatter images from the acquired projection images. The scatter free projection images are then post processed at step 86. The post processing may involve normalization and correction for bad pixels. The processed scatter free projection images are then reconstructed to generate a three-dimensional image of the object at step 88.

FIG. 7 illustrates, for a turbine fan blade, uncorrected image and scatter corrected images by employing control logic of FIG. 6. Image 90 is the uncorrected image obtained by a typical VCT system, while images 92 and 94 are scatter corrected images obtained by employing the scatter rejection plate and the control logic described via the flowchart 66. Further, it should be noted that image 92 is the scatter corrected image obtained by employing aperture plate, while image 94 is the scatter corrected image obtained by employing collimator plate.

It should be noted that one or more imaging parameters should be substantially maintained (that is, maintained at substantially similar values) for a particular imaging application and inspection requirement. Non-limiting examples of the imaging parameters include a type of object being imaged, a shape and an orientation of the object being imaged, projection angles from which the scatter images and subsequent projection images are acquired, an x-ray technique being employed, a geometry and one or more settings of the source and the detector, distance of the scatter rejection plates from the source and the detector, and so forth. For example, the above process may be set for imaging similar objects (e.g., turbine blades). The objects should be mounted on the turntable at substantially similar orientations. Further, the distance of the scatter rejection plate from the source and the detector should be substantially maintained while acquiring and storing the scatter images for each of the predetermined projection angles. In one embodiment, this may be achieved by coupling or attaching the scatter rejection plate to the two-dimensional flat panel detector array. Additionally, projection images should be acquired for projection angles for which the scatter images have been generated and stored. Moreover, the x-ray technique employed, the geometry and other settings for the source and the detector should be maintained at substantially similar values, such that the beam shape and intensity are same for various image acquisitions.

As will be appreciated by those skilled in the art, the scatter correction techniques described in the various embodiments discussed above permit a measurement of the scatter content in the projection images used for VCT imaging and correct the projection images, thereby improving the VCT image quality. The technique permits measurement of scatter content in x-ray images for a given geometry, scanning orientation, and x-ray technique prior to a VCT scan and use it during an actual imaging scan. This improves the throughput of the VCT system since scatter correction for the projection images is then a simple image subtraction process. Further, as will be appreciated by those skilled in the art, it is easier to measure primary radiation than the scatter radiation and positioning the scatter rejection plate between the object and the detector makes the measurement of primary radiation substantially convenient. Additionally, the use of narrow collimators permits the imaging of the higher spatial frequency content of the scatter images. Moreover, the technique permits capture and correction of the beam scatter (scatter due to the imaged object) as well as the background radiation scatter (scatter due to external object).

Further, as will be appreciated by those skilled in the art, the technique may be employed as a part of the system calibration process prior to the actual imaging application. Typically, prior to performing VCT imaging for metrology or inspection, an operator has to perform a few system calibration steps such as, flat field calibration of the detector, bad pixel test and calibration of the detector, geometrical alignment and calibration of the system. The scatter correction technique described in the embodiments discussed above may similarly become a part of the calibration process where the scatter images will be obtained for a specific object and stored prior to the performance of an actual metrology or inspection process.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for imaging an object, the method comprising:
acquiring a first projection image of the object using a source and a detector, the first projection image comprising a primary image of the object and a scatter image of the object;
positioning a scatter rejection plate between the object and the detector;
acquiring a second projection image of the object with the scatter rejection plate disposed between the object and the detector, the second projection image comprising the primary image of the object;
generating a scatter image of the object based on the first projection image and the second projection image; and
storing the scatter image of the object for subsequent imaging, wherein subsequent imaging includes reconstructing a three-dimensional image of the object based on a scatter free projection image by subtracting the scatter image of the object from the projection images in a single subtraction process step.

2. The method of claim 1, wherein generating the scatter image further comprises generating a scatter grid image by subtracting the second projection image from the first projection image.

3. The method of claim 2, wherein generating the scatter image further comprises detecting a plurality of aperture points for the scatter grid image and interpolating the scatter grid image based on the aperture points.

4. The method of claim 1, wherein the scatter image is stored for each of a plurality of projection angles.

5. The method of claim 1, wherein subsequent imaging comprises acquiring a plurality of projection images of the object from a plurality of projection angles.

6. The method of claim 5, wherein subsequent imaging comprises generating a plurality of scatter free projection images based on the projection images and respective scatter images.

7. The method of claim 5, wherein reconstructing comprises normalizing and correcting at least one bad pixel in a plurality of scatter free projection images.

8. The method of claim 1, further comprising maintaining a plurality of substantially similar imaging parameters.

9. The method of claim 8, wherein the imaging parameters are selected from the group consisting of a type of object being imaged, a shape and an orientation of the object being imaged, projection angles from which the scatter images and subsequent projection images are acquired, an x-ray technique being employed, a geometry and one or more settings of the source and the detector, and combinations thereof.

10. The method of claim 1, wherein the scatter rejection plate is designed based on a type of imaging application so as to optimize scatter rejection performance.

11. The method of claim 1, wherein the scatter rejection plate comprises at least one of an aperture plate or a collimator plate.

12. The method of claim 11, wherein the aperture plate comprises a high density material and defines a plurality of sub-centimeter sized circular apertures.

13. The method of claim 11, wherein the collimator plate comprises a high density material and defines a plurality of sub-centimeter sized horizontal or vertical slots.

14. A method for imaging an object, the method comprising:
- acquiring a plurality of projection images of the object using a source and a detector oriented at a plurality of projection angles relative to the object;
- generating a plurality of scatter free projection images by correcting the plurality of projection images based on respective ones of a plurality of stored scatter images by subtracting the scatter images from the respective projection images in a single process step, wherein the scatter images are generated and stored for each of the projection angles by positioning a scatter rejection plate between the object and the detector and wherein the step of generating the scatter images for each of the respective projection angles comprises;
  - acquiring a first projection image of the object, the first projection image comprising a primary image of the object and the scatter image of the object;
  - positioning the scatter rejection plate between the object and the detector;
  - acquiring a second projection image of the object with the scatter rejection plate disposed between the object and the detector, the second projection image comprising the primary image of the object; and
  - generating the scatter image of the object based on the first projection image and the second projection image; and
- reconstructing a three-dimensional image of the object based on the scatter free projection images.

15. A volumetric CT system for imaging an object, the system comprising:
- a source and a detector configured to move with respect to the object, wherein the detector is further configured to acquire a plurality of projection images of the object from a plurality of projection angles; and
- a processor configured to generate a plurality of scatter free projection images in a single process step by correcting the projection images based on respective stored scatter images by subtracting the scatter images from the respective projection images and to reconstruct a three-dimensional image of the object based on the scatter free projection images, wherein the scatter images are generated and stored for each of the projection angles by employing a scatter rejection plate positioned between the object and the detector.

16. The system of claim 15, wherein for each of the projection angles, the detector is further configured to acquire a first projection image of the object and a second projection image of the object with the scatter rejection plate positioned between the object and the detector, and wherein the processor is further configured to generate the scatter image of the object at the respective one of the projection angles based on the first projection image and the second projection image.

17. The system of claim 15, wherein the scatter rejection plate is designed based on a type of imaging application so as to optimize scatter rejection performance.

18. The system of claim 15, wherein the scatter rejection plate comprises at least one of an aperture plate or a collimator plate.

* * * * *